(12) United States Patent
Oh et al.

(10) Patent No.: US 11,197,608 B2
(45) Date of Patent: Dec. 14, 2021

(54) EYE DISEASE DIAGNOSIS METHOD AND SYSTEM USING ARTIFICIAL INTELLIGENCE

(71) Applicants: Samsung Life Public Welfare Foundation, Seoul (KR); Research & Business Foundation Sungkyunkwan University, Suwon-si (KR)

(72) Inventors: Sei Yeul Oh, Seoul (KR); Kyung Ah Park, Seoul (KR); Baek Hwan Cho, Seoul (KR)

(73) Assignees: SAMSUNG LIFE PUBLIC WELFARE FOUNDATION, Seoul (KR); RESEARCH & BUSINESS FOUNDATION SUNGKYUNKWAN UNIVERSITY, Suwon-si (KR)

(\*) Notice: Subject to any disclaimer, the term of this patent is extended or adjusted under 35 U.S.C. 154(b) by 92 days.

(21) Appl. No.: 16/709,991

(22) Filed: Dec. 11, 2019

(65) Prior Publication Data

US 2020/0187775 A1 Jun. 18, 2020

(30) Foreign Application Priority Data

Dec. 12, 2018 (KR) .................. 10-2018-0159943

(51) Int. Cl.
*G06K 9/00* (2006.01)
*A61B 3/14* (2006.01)
(Continued)

(52) U.S. Cl.
CPC ............ *A61B 3/145* (2013.01); *A61B 5/7267* (2013.01); *G06T 7/0016* (2013.01); *G16H 30/20* (2018.01);
(Continued)

(58) Field of Classification Search
None
See application file for complete search history.

(56) References Cited

U.S. PATENT DOCUMENTS

2018/0214087 A1   8/2018   Balaji et al.
2019/0110753 A1\*  4/2019   Zhang .................. G16H 50/20

FOREIGN PATENT DOCUMENTS

KR       10-1848321 B1     4/2018

OTHER PUBLICATIONS

He ("Axial Length/Corneal Radius Ratio: Association with Refractive State and Roleon Myopia Detection Combined with Visual Acuity in Chinese Schoolchildren", PLos Med. Feb. 18, 2015, pp. 1-19). (Year: 2015).\*

\* cited by examiner

*Primary Examiner* — Wei Wen Yang
(74) *Attorney, Agent, or Firm* — Myers Bigel, P.A.

(57) ABSTRACT

An eye disease diagnosis method using artificial intelligence may include: collecting, from a database, a first eyeground image of a myopic patient who is not diagnosed with an eye disease and a second eyeground image of a myopic patient who has been diagnosed with the eye disease; learning eyeball change information by degree of myopia based on the first eyeground image, using deep learning; comparing and analyzing the first eyeground image and the second eyeground image based on the eyeball change information by the degree of myopia, and learning eyeball change information by the eye disease using deep learning; and estimating determination criteria of an eyeground image for diagnosis of the eye disease, based on a difference between the eyeball change information by the degree of myopia and the eyeball change information by the eye disease.

9 Claims, 5 Drawing Sheets

(51) Int. Cl.
*A61B 5/00* (2006.01)
*G06T 7/00* (2017.01)
*G16H 30/20* (2018.01)
*G16H 50/20* (2018.01)
(52) U.S. Cl.
CPC ... *G16H 50/20* (2018.01); *G06T 2207/20081* (2013.01); *G06T 2207/30041* (2013.01)

EYE DISEASE DIAGNOSIS METHOD AND SYSTEM USING ARTIFICIAL INTELLIGENCE

CROSS-REFERENCE TO RELATED APPLICATION

This U.S. non-provisional patent application claims priority under 35 U.S.C. § 119 to Korean Patent Application No. 10-2018-0159943, filed on Dec. 12, 2018, in the Korean Intellectual Property Office, the disclosure of which is incorporated herein in its entirety by reference.

BACKGROUND

1. Technical Field

The present disclosure relates to an eye disease diagnosis method and system using artificial intelligence, and more particularly, to an eye disease diagnosis method and system for diagnosing an eye disease based on a result obtained by comparing and learning eyeball change information by myopia and eyeball change information by an eye disease through deep learning for eyeground (i.e. fundus) images.

2. Related Art

Recently, technologies related to diagnosis of various eye diseases such as glaucoma and macular degeneration have continuously developed. Representative examples of the technologies may include a technology for automatically diagnosing a patient's eye disease using the result of an optic nerve examination, optical coherence tomography or visual field examination (ex. US Patent Application Publication No. 2017-0357879 and the like).

However, such conventional technologies related to diagnosis of eye diseases may mistake a change in eyeball by myopia for a change in eyeball by an eye disease or may not normally identify the change in eyeball by myopia. That is, myopia may change the axial length, optic nerve or retinal morphologies. Due to such a change, a dark spot may be formed in the visual field examination, and a measurement value of the optical coherence tomography may vary. Therefore, the conventional technologies may not accurately diagnose an eye disease.

Therefore, examination results of myopic patients are excluded from categories in which eye diseases can be automatically diagnosed through modern medical technology, and diagnoses of eye diseases of myopic patients inevitably rely on the experiences and subjective judgments of clinicians.

RELATED ART DOCUMENT

Patent Document

1. US Patent Publication No. 2017-0357879 (Dec. 14, 2017)

SUMMARY

Various embodiments are directed to a method and system which can compare and analyze eyeball change information by myopia and eyeball change information by an eye disease through deep learning for eyeground images, and thus minimize misdiagnosis by an eyeball change caused by myopia during an eye disease diagnosis process.

In an embodiment, an eye disease diagnosis method using artificial intelligence may include: collecting, from a database, a first eyeground image of a myopic patient who is not diagnosed with an eye disease and a second eyeground image of a myopic patient who has been diagnosed with the eye disease; learning eyeball change information by degree of myopia based on the first eyeground image, using deep learning; comparing and analyzing the first eyeground image and the second eyeground image based on the eyeball change information by the degree of myopia, and learning eyeball change information by the eye disease using deep learning; and estimating determination criteria of an eyeground image for diagnosis of the eye disease, based on a difference between the eyeball change information by the degree of myopia and the eyeball change information by the eye disease.

The eyeball change information by the degree of myopia may include one or more of twisted optic nerve, myopic maculopathy and peripapillary atrophy.

The eyeball change information by the eye disease may include one or more of the border thickness and shape of an optic nerve disc, the color of optic nerves, the shape of macula and peripapillary atrophy.

The eye disease diagnosis method may further include analyzing an eyeground image of a test subject based on the determination criteria and diagnosing an eye disease of the test subject, when the eyeground image of the test subject is inputted.

In an embodiment, an eye disease diagnosis system using artificial intelligence may include: a data collection unit configured to collect, from a database, a first eyeground image of a myopic patient who is not diagnosed with an eye disease and a second eyeground image of a myopic patient who has been diagnosed with the eye disease; a first deep learning unit configured to learn eyeball change information by degree of myopia based on the first eyeground image, using deep learning; a second deep learning unit configured to compare and analyze the first eyeground image and the second eyeground image based on the eyeball change information by the degree of myopia, and learn eyeball change information by the eye disease using deep learning; and a determination criteria estimation unit configured to estimate determination criteria of an eyeground image for diagnosis of the eye disease, based on a difference between the eyeball change information by the degree of myopia and the eyeball change information by the eye disease.

The eye disease diagnosis system may further include an eye disease diagnosis unit configured to analyze an eyeground image of a test subject based on the determination criteria and diagnose an eye disease of the test subject, when the eyeground image of the test subject is inputted through the data collection unit.

In an embodiment, there is provided a computer-readable recording medium which stores a program for implementing the above-described method.

In accordance with the embodiments of the present disclosure, the eye disease diagnosis method and system may not rely on subjective judgments of clinicians, but can automatically diagnose eye diseases of test subjects including myopic patients according to learning results through deep learning even though only eyeground images of the test subjects are inputted, thereby obtaining objectified eye disease diagnosis results.

Furthermore, the eye disease diagnosis method and system may not derive a diagnosis result of an eye disease according to standardized image analysis, but can diagnose an eye disease by learning results obtained by comparing and analyzing eyeball change information by myopia and eyeball change information by an eye disease, and thus minimize misdiagnosis for an eye disease by myopia. Therefore, the eye disease diagnosis method and system can further improve the accuracy and reliability of the diagnosis results.

DETAILED DESCRIPTION

Figure 1:
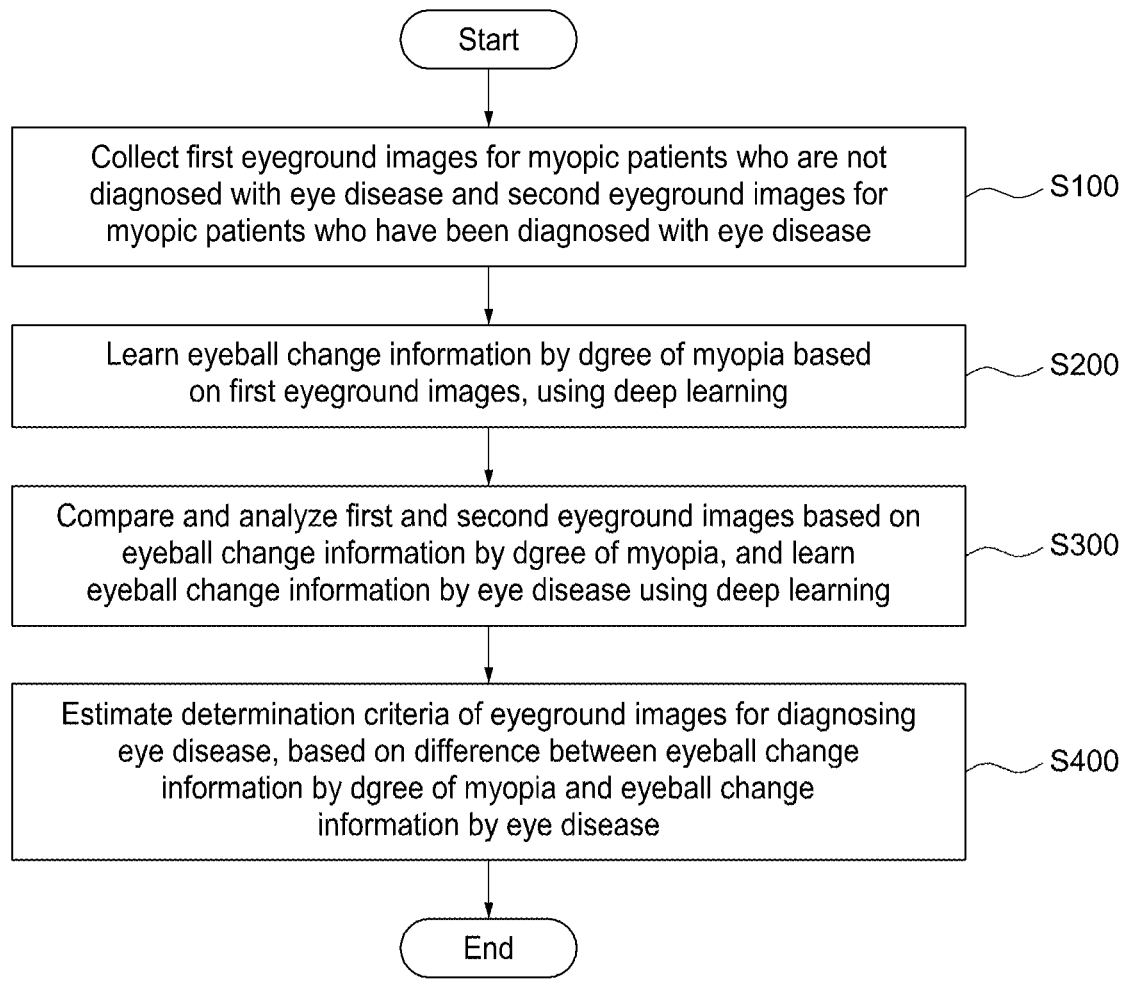
FIG. 1 is a first flowchart illustrating an eye disease diagnosis method using artificial intelligence in accordance with an embodiment of the present disclosure.

The terms used in this specification will be briefly described, and the present disclosure will be described in detail.

In this specification, general terms which are used at the moment as widely as possible in consideration of functions in the present disclosure are selected as the terms used in the present disclosure. However, the terms may be changed according to the appearance of new technologies, the precedents or the intentions of technicians working in the art to which the present disclosure pertains. In a specific case, there may be a term which has been randomly selected by the applicant. In this case, the meaning of the term will be described in detail in Detailed Description of this specification. Therefore, the definitions of the terms used herein should not be made by the names of the terms, but be made by the meanings of the terms based on the overall disclosures set forth herein.

Throughout the specification, when an element "includes" a component, it may indicate that the element does not exclude another component unless referred to the contrary, but can further include another component. The terms such as " . . . unit" and " . . . er" in this specification may indicate a unit for processing one or more functions or operations, and the unit may be embodied in hardware, software or a combination of hardware and software.

Hereafter, exemplary embodiments of the present disclosure will be described in detail with reference to the accompanying drawings, such that the present disclosure can be easily carried out by those skilled in the art to which the present disclosure pertains. However, the present disclosure can be embodied in various forms, and are not limited to the embodiments. In the drawings, components which have nothing to do with the description will be omitted in order to clearly describe the present disclosure. Throughout the specification, similar components will be represented by like reference numerals.

Hereafter, the present disclosure will be described in detail with reference to the accompanying drawings.

FIG. 1 is a first flowchart illustrating an eye disease diagnosis method using artificial intelligence in accordance with an embodiment of the present disclosure, showing a data collection and learning process for final eye disease diagnosis.

Figure 2A:
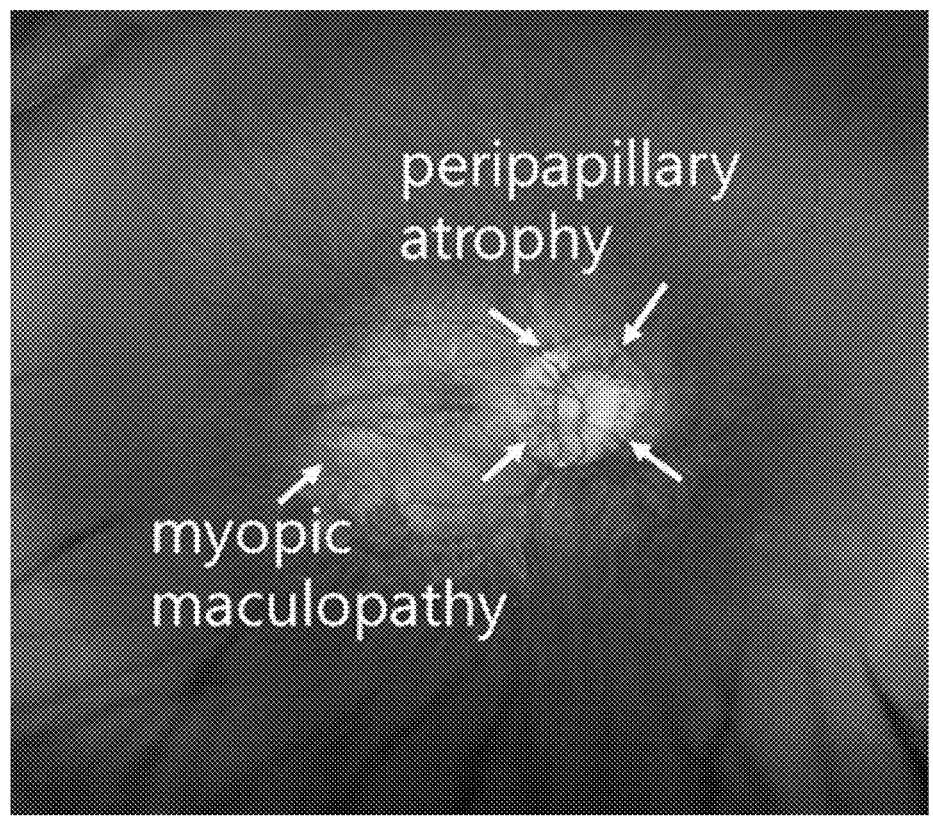
FIG. 2A is an eyeground image showing a change in eyeball by degree of myopia for a myopic patient who is not diagnosed with an eye disease.
Figure 2B:
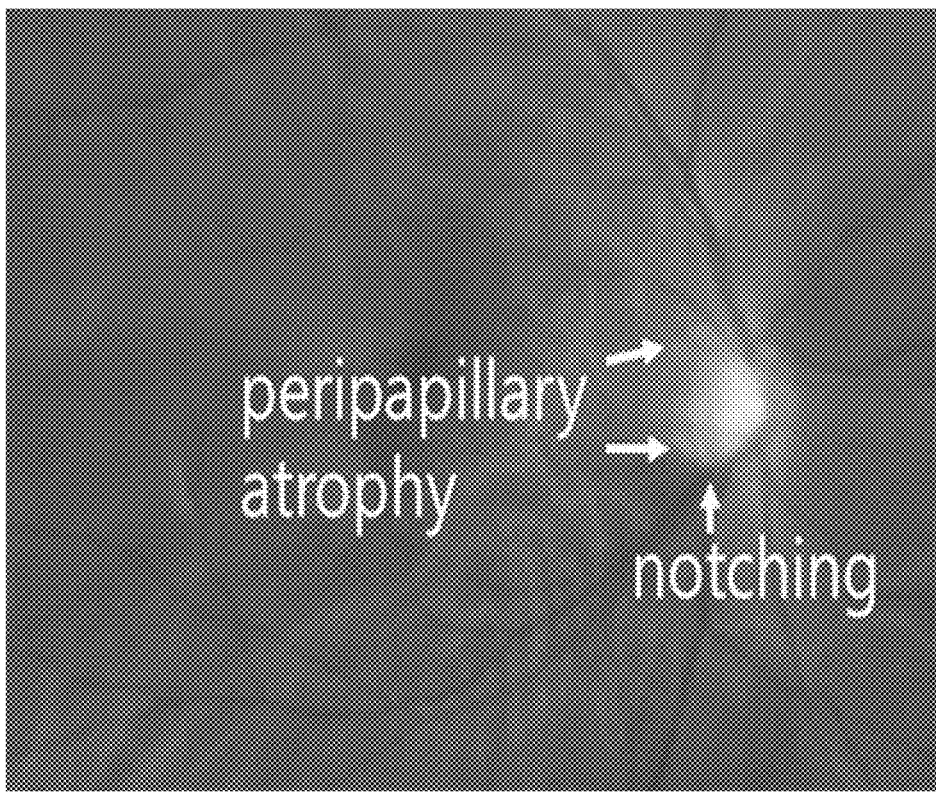
FIG. 2B is an eyeground image showing a change in eyeball by degree of myopia and eye disease for the myopia patent who has been diagnosed with the eye disease.

FIG. 2A is an eyeground image showing a change in eyeball by degree of myopia for a myopic patient who is not diagnosed with an eye disease, and FIG. 2B is an eyeground image showing a change in eyeball by degree of myopia and eye disease for the myopia patent who has been diagnosed with the eye disease.

Referring to FIG. 1, the eye disease diagnosis method using artificial intelligence in accordance with the embodiment of the present disclosure may include: collecting, from a database 200, first eyeground images for myopic patients who are not diagnosed with an eye disease and second eyeground images for myopic patients who have been diagnosed with an eye disease (step S100); learning information on a change in eyeball (hereafter referred to as eyeball change information) by degree of myopia based on the first eyeground images, using deep learning (step S200); comparing and analyzing the first and second eyeground images based on the eyeball change information by the degree of myopia, and learning the eyeball change information by the eye disease using deep learning (step S300); and estimating determination criteria for eyeground images for diagnosing the eye disease based on a difference between the eyeball change information by the degree of myopia and the eyeball change information by the eye disease (step S400).

In accordance with the embodiment of the present disclosure, in the eyeground image collection step S100, all eyeground images of myopic patients may be collected from the database 200 by a data collection unit 10. At this time, an eyeground image of a myopic patient who is not diagnosed with an eye disease among the myopic patients may be collected as the first eyeground image, and an eyeground image of a myopic patient who has been diagnosed with the eye disease among the myopic patients may be collected as the second eyeground image.

That is, the data collection unit 10 may sort and collect the eyeground images of the myopic patients according to whether the myopic patients have been diagnosed with the eye disease. The collected eyeground images may be sorted into the first eyeground images and the second eyeground images, according to whether the myopic patients have been diagnosed with the eye disease. The reason to sort and collect the eyeground images according to whether the myopic patients have been diagnosed with the eye disease, in the eyeground image collection step, is in order to control a deep learning unit to accurately learn the eyeball change information by the degree of myopia and the eyeball change information by the eye disease.

The database 200 may include not only a database within a hospital which uses a system 100 in accordance with an embodiment of the present disclosure, but also an accessible database of an external organization.

When the collecting of the eyeground images is completed in accordance with the embodiment of the present disclosure, a first deep learning unit 20 may learn the eyeball change information by the degree of myopia based on the first eyeground images, in the step S200. That is, the first deep learning unit 20 may learn changes in eyeballs, which appear depending on the degree of myopia, from the eyeground images of the myopic patients who are not diagnosed with the eye disease, through image analysis FIG. 2A, which is an eyeground image of a 42-year-old patient with an excessive myopia of −23.5 diopters at his/her right eyeball, shows that peripapillary atrophy and myopic maculopathy are identified around the optic nerves of the eyeball of the highly myopic patient who is not diagnosed with an eye disease. The first deep learning unit 20 may learn the eyeball change information by the degree of myopia through a deep learning process for the first eyeground images.

The eyeball change information by the degree of myopia in accordance with the embodiment of the present disclosure may include one or more of twisted optic nerve, myopic maculopathy and peripapillary atrophy. The eyeball change information by the degree of myopia may include not only structural and biological changes of tissue within an eyeball by degree of myopia, but also a change of condition in eyeball by a myopic disease.

The twisted optic nerve, the myopic maculopathy and the peripapillary atrophy, which are the eyeball change information by the degree of myopia, are examples of the learning result. As the data collection step and the learning step in accordance with the embodiment of the present disclosure are repeated, the eyeball change information may be subdivided or added.

When the learning of the eyeball change information by the degree of myopia in accordance with the embodiment of the present disclosure is completed, a second deep learning unit 30 may compare and analyze the eyeground images based on the eyeball change information by the degree of myopia, and learn the eyeball change information by the eye disease according to the result of the comparison analysis, in step S300. That is, through the image analysis using deep learning, the second deep learning unit 30 may learn the plural pieces of eyeball change information by the eye disease, except the eyeball using deep learning.

For example, change information by the degree of myopia, among the plural pieces of eyeball change information by the myopia and the eye disease in the eyeground images of the myopic patients who have been diagnosed with the eye disease.

For example, FIG. 2B, which is an eyeground image of a 42-year-old patient who had a refractive surgery due to an excessive myopia at his/her right eyeball and has been diagnosed with glaucoma, shows that notching of an optic disc rim as well as peripapillary atrophy is identified in the eyeball of the myopic patient who has been diagnosed with glaucoma (i.e. eye disease). Compared to the result checked through FIG. 2A, the peripapillary atrophy may be estimated as the eyeball change information by the degree of myopia, not the eye disease. Therefore, the second deep learning unit 30 may learn that the notching of the optic disc rim is the eyeball change information by the eye disease, through the deep learning process.

When the eyeball change information by the degree of myopia and the eyeball change information by the eye disease are identified in a same tissue within the eyeball or identified in similar shapes during the comparison analysis process of the first and second eyeground images, the second deep learning unit 30 may learn the eyeball change information by the eye disease by comparing and analyzing a difference in extent, range or numerical value between the eyeball changes which are determined to be the same as or similar to each other.

For example, when the results obtained by learning the eyeball change information by the degree of myopia and the eyeball change information by the eye disease show that peripapillary atrophy has been commonly learned as the eyeball change information, the second deep learning unit 30 may analyze the first and second eyeground images based on changes of area on the eyeground images for the extent of the peripapillary atrophy, and learn a difference between the eyeball change information by the degree of myopia and the eyeball change information by the eye disease.

The eyeball change information by the eye disease in accordance with the embodiment of the present disclosure may include one or more of the border thickness and shape of an optic nerve disc, the color of optic nerves, the shape of macula or the peripapillary atrophy. The eyeball change information by the eye disease may include a structural change, biological change and change of condition in tissues within an eyeball, caused by the eye disease, except the eyeball changes by the degree of myopia.

The border thickness and shape of an optic nerve disc, the color of optic nerves, the shape of macula and the peripapillary atrophy, which are the above-described eyeball change information by the eye disease, are examples of the learning result. As the data collection step and the learning step in accordance with the embodiment of the present disclosure are repeated, the eyeball change information may be subdivided or added.

In accordance with the embodiment of the present disclosure, in the determination criteria estimation step S400, a determination criteria estimation unit may estimate determination criteria for the eyeground images based on the eyeball change information by the eye disease. The determination criteria refer to reference values which are used to analyze eyeground images based on the eyeball change information by the eye disease in order to diagnose an eye disease.

For example, the determination criteria may include information on whether the border thickness and shape of an optic nerve disc have been changed in comparison to that in a normal state, information on whether the color of optical nerve has been changed in comparison to that in a normal state, information on whether the shape of macula has been changed in comparison to that in a normal state, and information on whether the periphery of the optic nerve disc has atrophied by a predetermined area range value. At this time, a determination criteria estimation unit 40 may estimate a predetermined value (ex. predetermined area range value) serving as a reference value for the respective pieces of eyeball change information based on a difference between the eyeball change information by the degree of myopia and the eyeball change information by the eye disease.

Figure 3:
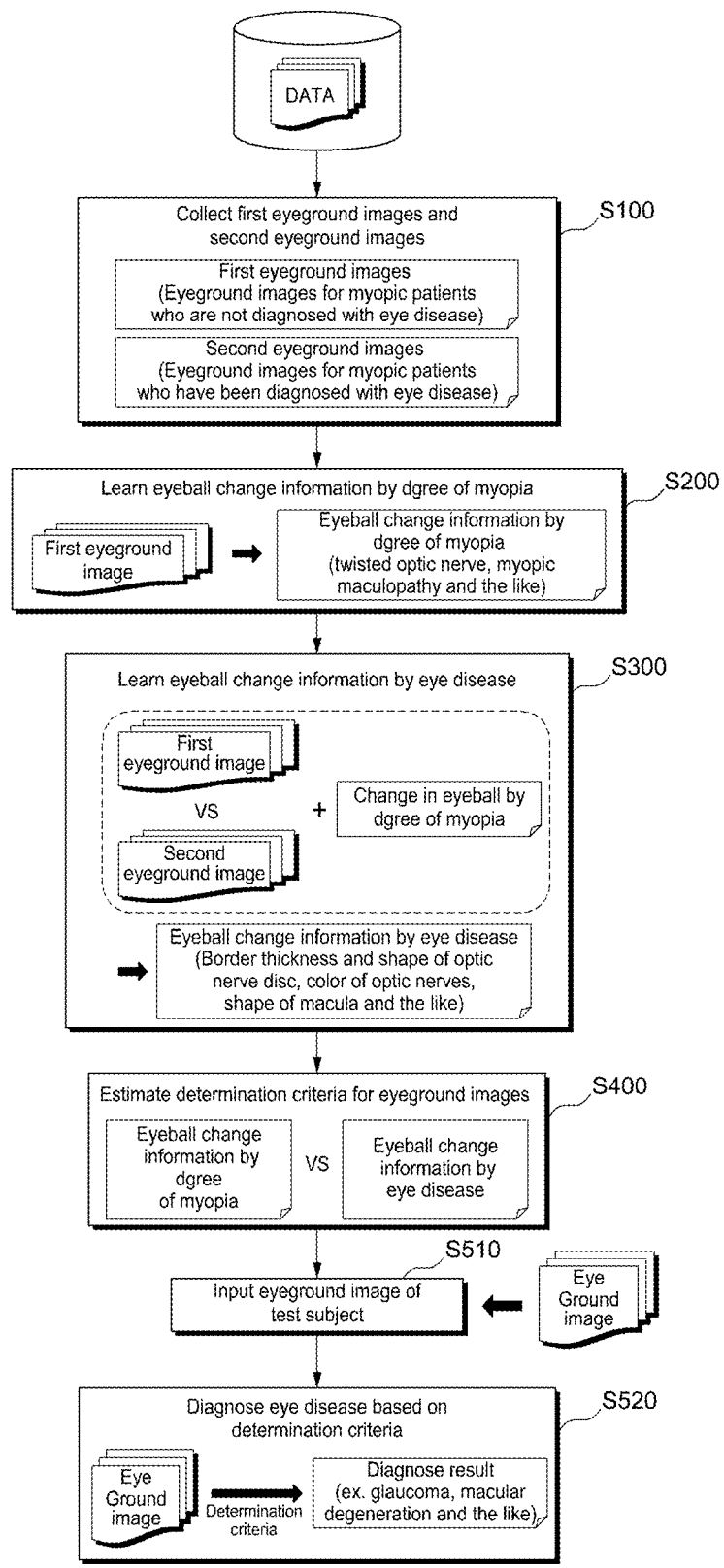
FIG. 3 is a second flowchart illustrating an eye disease diagnosis method using artificial intelligence in accordance with an embodiment of the present disclosure.

FIG. 3 is a second flowchart illustrating an eye disease diagnosis method using artificial intelligence in accordance with an embodiment of the present disclosure, showing the entire processes including a data collection process, a learning process and an eye disease diagnosis process.

Referring to FIG. 3, the eye disease diagnosis method using artificial intelligence in accordance with the embodiment of the present disclosure may further include analyzing an eyeground image of a test subject based on the determination criteria and diagnosing an eye disease of the test subject, when the eyeground image of the test subject is inputted, in steps S510 and S520. The test subject refers to a patient who is to be diagnosed with whether the patient has an eye disease.

The eyeground image of the test subject in accordance with the embodiment of the present disclosure may be directly inputted to the data collection unit 10 by an external input applied from a clinician or the like, or transferred from a user device 300 or a database of a test device and then inputted to the data collection unit 10, in step S510.

When the eyeground image of the test subject in accordance with the embodiment of the present disclosure is inputted to the data collection unit 10, an eye disease diagnosis unit 50 may analyze the input eyeground image of the test subject according to the determination criteria estimated by the determination criteria estimation unit 40, and diagnose an eye disease according to the analysis result, in step S520.

For example, the eye disease diagnosis unit 50 may analyze whether the border thickness and shape of an optic nerve disc have been changed in comparison to that in a normal state, and whether the periphery of the optic nerve disc has atrophied by a predetermined area range value, for the eyeground image of the test subject. When the analysis result indicates that the test subject has an eye disease, the eye disease diagnosis unit 50 may determine which kind of eye disease (ex. glaucoma or macular degeneration) the test subject has.

The eye disease diagnosis method in accordance with the embodiment of the present disclosure can minimize misdiagnosis of an eye disease caused by the myopia, among factors having an influence on a change in eyeball, and accurately determine whether the test subject has an eye disease and which kind of eye disease the test subject has, based on the changes in eyeball by the eye disease, which have been learned based on the eyeground images of the myopic patients.

Figure 4:
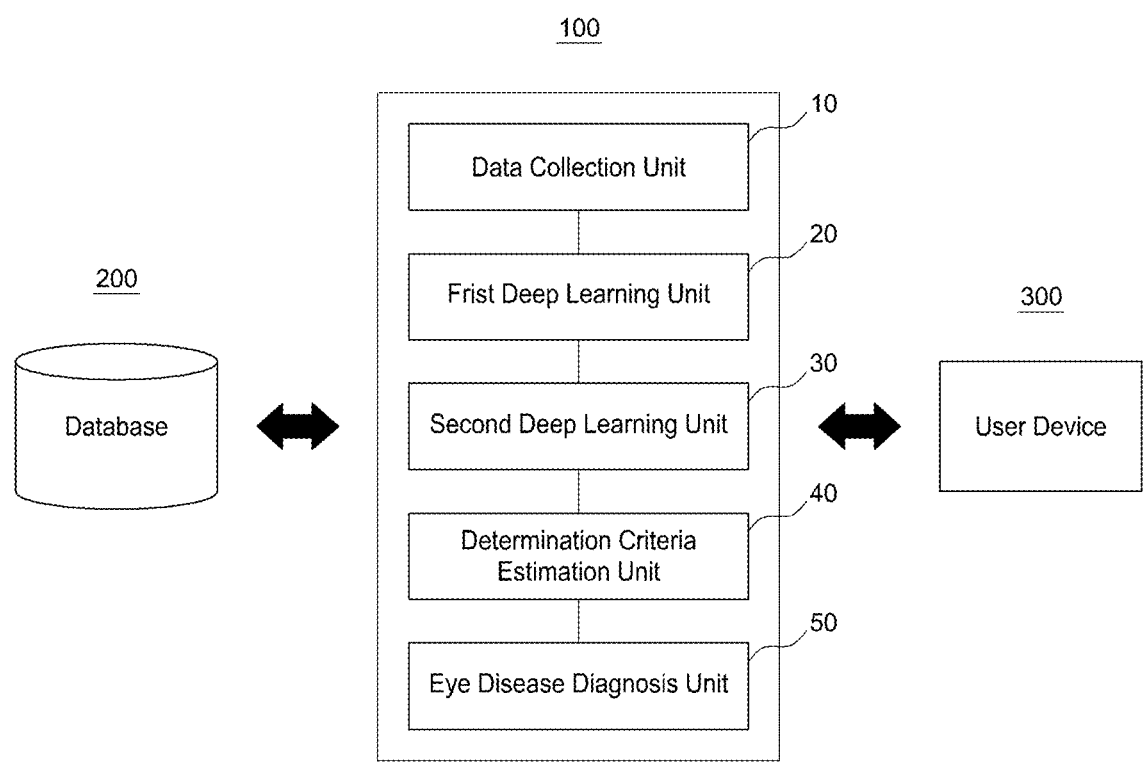
FIG. 4 is a block diagram illustrating an eye disease diagnosis system using artificial intelligence in accordance with an embodiment of the present disclosure.

FIG. 4 is a block diagram illustrating the eye disease diagnosis system 100 using artificial intelligence in accordance with an embodiment of the present disclosure.

Referring to FIG. 4, the eye disease diagnosis system 100 using artificial intelligence in accordance with the embodiment of the present disclosure may include the data collection unit 10, the first deep learning unit 20, the second deep learning unit 30, the determination criteria estimation unit 40 and the eye disease diagnosis unit 50. The data collection unit 10 may collect, from the database 200, first eyeground images of myopic patients who are not diagnosed with an eye disease and second eyeground images of myopic patients who have been diagnosed with an eye disease. The first deep learning unit 20 may learn eyeball change information by degree of myopia based on the first eyeground images, using deep learning. The second deep learning unit 30 may compare and analyze the first and second eyeground images based on the eyeball change information by the degree of myopia, and learn eyeball change information by the eye disease using deep learning. The determination criteria estimation unit 40 may estimate determination criteria for eyeground images for diagnosing the eye disease, based on a difference between the eyeball change information by the degree of myopia and the eyeball change information by the eye disease. The eye disease diagnosis unit 50 may analyze an eyeground image of a test subject based on the determination criteria, and diagnose an eye disease of the test subject, when the eyeground image of the test subject is inputted through the data collection unit 10.

Referring to FIG. 4, the system 100 in accordance with the embodiment of the present disclosure may be interconnected with the user device 300. The user device 300 is a device which can perform wired/wireless network communication, and may include a smartphone, PMP (Portable Multimedia Player), PDA (Personal Digital Assistant), desktop PC, laptop PC, tablet PC and the like.

As the system 100 in accordance with the embodiment of the present disclosure is interconnected with the user device 300, the data collection unit 10 may receive an eyeground image of the test subject from the user device 300. The system 100 in accordance with the embodiment of the present disclosure may output information on eye disease diagnosis through the user device 300.

The contents of the above-described method may be applied to the system 100 in accordance with the embodiment of the present disclosure. Therefore, the descriptions of the same contents of the system 100 as those of the above-described method are omitted herein.

In accordance with an embodiment of the present disclosure, it is possible to provide a computer-readable recording medium which stores a program for executing the above-described method in a computer. In other words, the above-described method may be created as a program which can be executed in a computer, and implemented in a general-purpose digital computer that operates the program using a computer-readable medium. The structure of data used in the above-described method may be recorded into a computer-readable medium through various units. However, it should not be understood that the recording medium for recording an executable computer program or code for performing the various methods of the present disclosure includes temporary targets such as carrier waves or signals. The computer-readable medium may include storage media such as magnetic storage media (ex. ROM, floppy disk, hard disk and the like) and optical readable media (ex. CD ROM, DVD and the like).

The descriptions of the present disclosure are only examples, and it should be understood that the present disclosure can be easily modified into other specific forms by those skilled in the art to which the present disclosure pertains, without changing the technical spirit or necessary features of the present disclosure. Therefore, it should be understood that the above-described embodiments are illustrative only in all aspects and are not limitative. For example, components described in a singular form may be carried out in a distributed form. Similarly, distributed components may be carried out in a coupled form.

The scope of the present disclosure may be defined by the following claims rather than the detailed descriptions, and it should be interpreted that the meanings and scope of the claims and all changes or modifications derived from the equivalents thereto are included in the scope of the present disclosure.

What is claimed is:

1. An eye disease diagnosis method using artificial intelligence, the eye disease diagnosis method comprising:
   collecting separately, from a database, a first eyeground image of a myopic patient who is not diagnosed with an eye disease and a second eyeground image of a myopic patient who has been diagnosed with the eye disease;
   learning optic nerve change information by degree of myopia based on the first eyeground image, using deep learning;
   comparing and analyzing the first eyeground image of a myopic patient who is not diagnosed with an eye disease and the second eyeground image of a myopic patient who has been diagnosed with an eye disease based on the optic nerve change information by the degree of myopia, and learning optic nerve change information by the eye disease using deep learning; and
   estimating determination criteria of an eyeground image for diagnosis of the eye disease, based on a difference between the optic nerve change information by the degree of myopia and the optic nerve change information by the eye disease,
   wherein the eye disease is an optic nerve disease.

2. The eye disease diagnosis method of claim 1, wherein the optic nerve change information by the degree of myopia comprises one or more of twisted optic nerve or peripapillary atrophy.

3. The eye disease diagnosis method of claim 1, wherein the optic nerve change information by the eye disease comprises one or more of a border thickness and shape of an optic nerve disc, a color of optic nerves, or peripapillary atrophy.

4. The eye disease diagnosis method of claim 1, further comprising analyzing an eyeground image of a test subject based on the determination criteria and diagnosing an eye disease of the test subject, when the eyeground image of the test subject is inputted.

5. An eye disease diagnosis system using artificial intelligence, the eye disease diagnosis system comprising:
 a data collection unit configured to collect separately, from a database, a first eyeground image of a myopic patient who is not diagnosed with an eye disease and a second eyeground image of a myopic patient who has been diagnosed with the eye disease;
 a first deep learning unit configured to learn optic nerve change information by degree of myopia based on the first eyeground image, using deep learning;
 a second deep learning unit configured to compare and analyze the first eyeground image and the second eyeground image based on the optic nerve change information by the degree of myopia, and learn optic nerve change information by the eye disease using deep learning; and
 a determination criteria estimation unit configured to estimate determination criteria of an eyeground image for diagnosis of the eye disease, based on a difference between the optic nerve change information by the degree of myopia and the optic nerve change information by the eye disease,
 wherein the data collection unit, the first deep learning unit, the second deep learning unit, and the determination criteria estimation unit comprise hardware, software, or a combination thereof.

6. The eye disease diagnosis system of claim 5, wherein the optic nerve change information by the degree of myopia comprises one or more of twisted optic nerve or peripapillary atrophy.

7. The eye disease diagnosis system of claim 5, wherein the optic nerve change information by the eye disease comprises one or more of a border thickness and shape of an optic nerve disc, a color of optic nerves, or peripapillary atrophy.

8. The eye disease diagnosis system of claim 5, further comprising an eye disease diagnosis unit configured to analyze an eyeground image of a test subject based on the determination criteria and diagnose an eye disease of the test subject, when the eyeground image of the test subject is inputted through the data collection unit,
 wherein the eye diagnosis unit comprises the hardware, the software, or the combination thereof.

9. A non-transitory computer-readable recording medium which stores a program for implementing the method of claim 1.

* * * * *